(12) United States Patent
Takata

(10) Patent No.: US 10,355,654 B2
(45) Date of Patent: Jul. 16, 2019

(54) AMPLIFIER CIRCUIT AND DETECTION APPARATUS INCLUDING THE SAME

(71) Applicant: Murata Manufacturing Co., Ltd., Kyoto (JP)

(72) Inventor: Masaaki Takata, Kyoto (JP)

(73) Assignee: MURATA MANUFACTURING CO., LTD., Kyoto (JP)

( * ) Notice: Subject to any disclaimer, the term of this patent is extended or adjusted under 35 U.S.C. 154(b) by 570 days.

(21) Appl. No.: 15/091,761

(22) Filed: Apr. 6, 2016

(65) Prior Publication Data

US 2016/0218687 A1 Jul. 28, 2016

Related U.S. Application Data

(63) Continuation of application No. PCT/JP2014/076746, filed on Oct. 7, 2014.

(30) Foreign Application Priority Data

Oct. 9, 2013 (JP) ................................. 2013-211782

(51) Int. Cl.
*H03F 3/45* (2006.01)
*A61B 5/08* (2006.01)
(Continued)

(52) U.S. Cl.
CPC ....... *H03F 3/45076* (2013.01); *A61B 5/0823* (2013.01); *A61B 5/11* (2013.01);
(Continued)

(58) Field of Classification Search
CPC ....... A61B 5/0823; A61B 5/11; A61B 5/7225; G01H 11/08
(Continued)

(56) References Cited

U.S. PATENT DOCUMENTS 4,752,053 A * 6/1988 Boetzkes ................ B61L 23/00
246/167 R
8,132,468 B2 * 3/2012 Radivojevic ............. G01L 1/16
73/777
(Continued)

FOREIGN PATENT DOCUMENTS

CN 103138696 A 6/2013
EP 1932473 A1 6/2008
(Continued)

OTHER PUBLICATIONS

Written Opinion for PCT/JP2014/076746 dated Jan. 13, 2015.
(Continued)

*Primary Examiner* — Tarun Sinha
(74) *Attorney, Agent, or Firm* — Pearne & Gordon LLP

(57) ABSTRACT

An amplifier circuit converts a charge signal into a voltage signal. The charge signal indicates a detection result outputted from a piezoelectric device that detects a detection object as a change in an amount of a charge. The charge signal includes a displacement signal in a predetermined frequency band. The amplifier circuit includes an operational amplifier including an inverting input terminal receiving the charge signal and an output terminal for outputting the voltage signal, a resistor electrically connected between the inverting input terminal and the output terminal, and a capacitor connected in parallel with the resistor. A resistance value of the resistor and a capacitance value of the capacitor are set such that, in the frequency band of the displacement signal, an absolute value of an impedance of the resistor is lower than an absolute value of an impedance of the capacitor.

8 Claims, 11 Drawing Sheets

(51) Int. Cl.
*A61B 5/11* (2006.01)
*A61B 5/00* (2006.01)
*G01H 11/08* (2006.01)
*A61B 7/04* (2006.01)
*G01P 15/09* (2006.01)

(52) U.S. Cl.
CPC .......... *A61B 5/4205* (2013.01); *A61B 5/7225* (2013.01); *G01H 11/08* (2013.01); *H03F 3/45475* (2013.01); *A61B 5/6893* (2013.01); *A61B 7/04* (2013.01); *G01P 15/0907* (2013.01); *H03F 2200/129* (2013.01); *H03F 2200/261* (2013.01); *H03F 2203/45512* (2013.01); *H03F 2203/45526* (2013.01); *H03F 2203/45528* (2013.01)

(58) Field of Classification Search
USPC .......................................................... 73/602
See application file for complete search history.

(56) References Cited

U.S. PATENT DOCUMENTS 8,456,450 B2 * 6/2013 Land ...................... H02M 7/06
 323/363

2004/0004781 A1 * 1/2004 Kobayashi ........... G11B 5/4806
 360/69

FOREIGN PATENT DOCUMENTS

| | | | | |
|---|---|---|---|---|
| JP | H01-240755 A | | 9/1989 | |
| JP | H01240755 A | * | 9/1989 | ............ F02D 45/00 |
| JP | H03-182109 A | | 8/1991 | |
| JP | H04-304008 A | | 10/1992 | |
| JP | H09-243655 A | | 9/1997 | |
| JP | 2006-340820 A | | 12/2006 | |
| JP | 2009-279122 A | | 12/2009 | |
| WO | 2007/040022 A1 | | 12/2007 | |

OTHER PUBLICATIONS

International Search report for PCT/JP2014/076746 dated Jan. 13, 2015.

Translation of Office action issued in JP2015-541578 dated May 31, 2016.

Translation of Written Opinion for PCT/JP2014/076746 dated Jan. 13, 2015.

Office action issued in Chinese Patent Application No. 201480055138.X dated Sep. 6, 2017.

* cited by examiner

CUTOFF FREQUENCY
fc > fmax

AMPLIFIER CIRCUIT AND DETECTION APPARATUS INCLUDING THE SAME

BACKGROUND OF THE DISCLOSURE

Field of the Disclosure

The present disclosure relates to an amplifier circuit and a detection apparatus including the same, and more specifically to an amplifier circuit that converts a charge signal into a voltage signal and to a detection apparatus including the amplifier circuit.

Description of the Related Art

Piezoelectric devices are used for the detection of, for example, vibration, torque, and weight. A piezoelectric device outputs a charge signal as a detection result. A charge amplifier circuit is used to convert the charge signal from a piezoelectric device into a voltage signal. Such a charge amplifier circuit is disclosed in, for example, Japanese Unexamined Patent Application Publication No. 3-182109 (Patent Document 1).

As an apparatus for detecting vibration, a detection apparatus that detects the state of a subject is proposed where the state of the subject is detected using a sensor attached to, for example, the body of the subject. For example, Japanese Unexamined Patent Application Publication No. 2009-279122 (Patent Document 2) discloses a state detection apparatus that detects swallowing or a cough of a subject.

Patent Document 1: Japanese Unexamined Patent Application Publication No. 3-182109.

Patent Document 2: Japanese Unexamined Patent Application Publication No. 2009-279122

BRIEF SUMMARY OF THE DISCLOSURE

Hereinafter, the problems found by the inventor will be described.

FIG. 14 is a circuit diagram illustrating an example of the configuration of a general charge amplifier circuit. Referring to FIG. 14, a charge amplifier circuit 90 converts a charge signal Qin from a piezoelectric device 1 into a voltage signal Vout. The frequency band of the charge signal Qin is, for example, 100 mHz to 10 Hz. The charge amplifier circuit 90 includes an operational amplifier U1, a resistor R1, a capacitor C1, and an output unit O1.

The operational amplifier U1 includes an inverting input terminal, a non-inverting input terminal, and an output terminal. The piezoelectric device 1 is electrically connected between the inverting input terminal and the non-inverting input terminal of the operational amplifier U1. The inverting input terminal receives the charge signal Qin from one end of the piezoelectric device 1. The non-inverting input terminal and the other end of the piezoelectric device 1 are electrically connected to a reference potential Vref. The voltage signal Vout is outputted from an output terminal.

The resistor R1 is electrically connected between the inverting input terminal and the output terminal of the operational amplifier U1. The capacitor C1 is connected in parallel with the resistor R1.

The resistance value of the resistor R1 is, for example, 50 MΩ. The capacitance value of the capacitor C1 is, for example, 10 nF. Hence, a time constant $\tau$ of the charge amplifier circuit 90 is calculated as $\tau = R1 \times C1 = 0.5$ s.

In the charge amplifier circuit 90, the charge signal Qin flows through the capacitor C1 and, hence, a charge is stored in the capacitor C1. Since a low-frequency signal can hardly pass through a capacitor, the charge amplifier circuit 90 has the frequency characteristics of a high pass filter (HPF). The cutoff frequency fc of this HPF is about $fc = 1/2\pi\tau = 300$ mHz.

FIG. 15 is a diagram illustrating examples of the frequency characteristics of the charge gain and the frequency characteristics of the group delay of the charge amplifier circuit 90 illustrated in FIG. 14. Referring to FIG. 15, the horizontal axis represents the frequency of the charge signal Qin using a logarithmic scale. The vertical axes represent the charge gain (the ratio of the voltage value of the voltage signal Vout to the amount of the charge of the charge signal Qin, refer to the left vertical axis) and the group delay of the voltage signal Vout with respect to the charge signal Qin (refer to the right vertical axis). A curve 15a represents the frequency characteristics of the charge gain. A curve 15b represents the frequency characteristics of the group delay.

In the example illustrated in FIG. 15, the frequency band of the charge signal Qin is 100 mHz to 10 Hz. The cutoff frequency fc of the charge amplifier circuit 90 is 300 mHz. In other words, the cutoff frequency fc is included within the frequency band of the charge signal Qin.

The group delay steeply changes at frequencies near the cutoff frequency. In the case where the frequency of the charge signal Qin is 100 mHz, the group delay is about 450 ms. On the other hand, in the case where the frequency of the charge signal Qin is 10 Hz, the group delay is about zero. Thus, the operation of the charge amplifier circuit is not ideal near the cutoff frequency fc and, hence, the responsiveness is poor depending on the frequency components included in the input charge signal Qin. Further, an output voltage waveform different from the waveform of an input charge signal may possibly be generated.

To solve this problem, a method is thought of in which the cutoff frequency fc is adjusted to a frequency lower than the frequency band of the charge signal Qin. This is because the frequency characteristics of the group delay become flat over the whole frequency band of the charge signal Qin when the cutoff frequency fc is made lower than the frequency band of the charge signal Qin.

However, the time constant $\tau$ needs to be increased to lower the cutoff frequency fc. In other words, it is necessary to increase the resistance value of the resistor R1 or the capacitance value of the capacitor C1.

A resistor having a high resistance value has a large size or high cost in many cases. Hence, there may be cases in which a resistor having such a high resistance value cannot be employed as the resistor R1.

On the other hand, in an ideal charge amplifier circuit, a charge gain is inversely proportional to the capacitance of the capacitor C1 (Vout/Qin=1/C1). In other words, the charge gain decreases as the capacitance value of the capacitor C1 is increased.

Further, when the time constant $\tau$ is increased, a time required for the activation of the charge amplifier circuit is increased.

Hence, the present disclosure has been made in order to solve such a problem, and it is an object of the present disclosure to provide a technique to improve the frequency characteristics of an amplifier circuit that amplifies a signal outputted from a charge output sensor.

An amplifier circuit according to an aspect of the present disclosure is an amplifier circuit that converts a charge signal into a voltage signal. The charge signal is outputted from a charge output sensor that detects a detection object, and the charge signal indicates a detection result as a change in an amount of a charge. The charge signal includes a first signal component in a predetermined frequency band. The amplifier circuit includes an operational amplifier, a resistor, and a capacitor. The operational amplifier includes an inverting input terminal receiving the charge signal and an output terminal for outputting the voltage signal. The resistor is electrically connected between the inverting input terminal and the output terminal. The capacitor connected in parallel with the resistor. A resistance value of the resistor and a capacitance value of the capacitor are set such that, in the frequency band of the first signal component, an absolute value of an impedance of the resistor is lower than an absolute value of an impedance of the capacitor. A cutoff frequency determined in accordance with a product of the resistance value and the capacitance value is set so as to be higher than the frequency band of the first signal component.

Preferably, the detection object is a movement of a living matter. The first signal component is a signal component in which an amount of a charge changes in accordance with the movement of the living matter.

Preferably, the charge signal further includes a second signal component whose frequency band is higher than the frequency band of the first signal component. The resistance value and the capacitance value are set such that, in the frequency band of the second signal component, the absolute value of the impedance of the capacitor is lower than the absolute value of the impedance of the resistor. The cutoff frequency is set so as to be lower than the frequency band of the second signal component.

Preferably, the second signal component is a signal component in which an amount of a charge changes in accordance with a sound generated by the movement of the living matter.

Preferably, the charge output sensor includes a first sensor and a second sensor. The amplifier circuit receives the first signal component from the first sensor and the second signal component from the second sensor.

A detection apparatus according to another aspect of the present disclosure includes the amplifier circuit described above and the charge output sensor.

Preferably, the frequency band of the first signal component is lower than a frequency of a commercial power supply. The frequency band of the second signal component is higher than the frequency of the commercial power supply. The detection apparatus further includes a low pass filter and a high pass filter. The low pass filter has a cutoff frequency lower than the frequency of the commercial power supply and allows the voltage signal in the frequency band of the first signal component to pass therethrough. The high pass filter has a cutoff frequency higher than the frequency of the commercial power supply and allows the voltage signal in the frequency band of the second signal component to pass therethrough.

Preferably, the charge output sensor includes a first sensor for outputting the first signal component and a second sensor for outputting the second signal component.

According to the present disclosure, the frequency characteristics of an amplifier circuit that amplifies a signal outputted from a charge output sensor can be improved.

DETAILED DESCRIPTION OF THE DISCLOSURE

Hereinafter, embodiments of the present disclosure will be described in detail with reference to the drawings. Note that identical portions or corresponding portions in the figures are denoted by the same reference symbols and duplicated descriptions thereof will not be repeated.

In the descriptions below, a piezoelectric device is shown as an illustrative form of a "charge output sensor (or first or second sensor)" in the present disclosure and the embodiments thereof. However, the "charge output sensor" according to the present disclosure is not limited to a piezoelectric device if the device is a sensor that detects a detection object and outputs a charge signal indicating the detection result as a change in the amount of a charge. The "charge output sensor" according to the present disclosure may be, for example, a pyroelectric device.

The "detection object" in the present disclosure and the embodiments thereof refers to the movement (for example, deformation or displacement) of a living matter or physical matter, a change in temperature, a change in pressure, or the like of a living matter or physical matter, causing a change in the amount of a charge to be generated in a charge output sensor. The embodiments of the present disclosure will illustrate a case in which the charge output sensor is a piezoelectric device and the detection object is the "movement of living matter". However, the detection object of the charge output sensor is not limited to the "movement of a living matter". For example, the charge output sensor may be a pyroelectric device and the detection object may be the change in temperature of physical matter or the change in the temperature of environment.

In the present disclosure and the embodiments thereof, the "movement of a living matter (or body movement)" refers to the movement of a living matter (for example, a subject) and a change in environment generated by the movement (for example, deformation, displacement, the change in weight of an object touched by the subject). Further, the living matter which is a detection object is not limited to a human being, and may be an animal other than a human being.

First Embodiment

Figure 1:
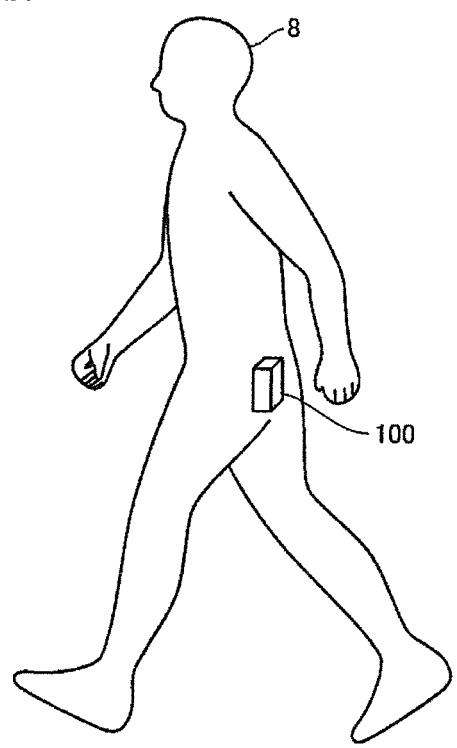
FIG. 1 is a schematic diagram illustrating the installation state of a detection apparatus according to a first embodiment of the present disclosure.

FIG. 1 is a schematic diagram illustrating the installation state of a body movement detection apparatus according to a first embodiment of the present disclosure. Referring to FIG. 1, a body movement detection apparatus 100 is mounted on, for example, a subject 8 and detects the body movement of the subject 8. Note that the "detection object" and the "detection result" of the piezoelectric device 1 correspond to the body movement of the subject 8.

Note that the position of the body movement detection apparatus 100 is a position near the waist of the subject 8 in FIG. 1, for convenience of illustration; however, the position of the body movement detection apparatus 100 may be appropriately set in accordance with the use.

Figure 2:
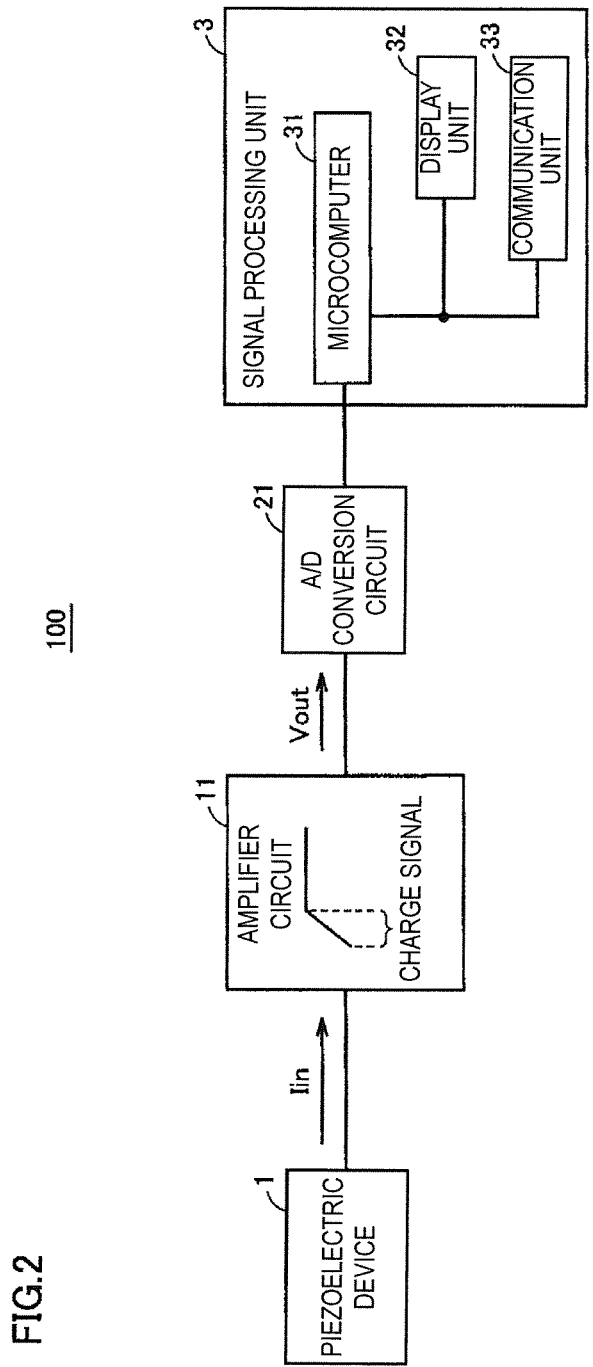
FIG. 2 is a block diagram schematically illustrating the configuration of the detection apparatus illustrated in FIG. 1.

FIG. 2 is a block diagram schematically illustrating the configuration of the body movement detection apparatus 100 illustrated in FIG. 1. Referring to FIG. 2, the body movement detection apparatus 100 includes the piezoelectric device 1, an amplifier circuit 11, an A/D (analog-digital) conversion circuit 21, and a signal processing unit 3.

The piezoelectric device 1 is deformed due to the body movement and outputs, to the amplifier circuit 11, a charge signal Iin indicating the amount of the deformation as a change in the amount of a charge. Publicly known configurations such as a mono-morph type, a bi-morph type, a multilayer type, and the like can be applied to the piezoelectric device 1, and the detailed descriptions thereof are not repeated here.

The amplifier circuit 11 amplifies the charge signal Iin from the piezoelectric device 1 and converts it into the voltage signal Vout. The configuration of the amplifier circuit 11 will be described in more detail later.

The A/D conversion circuit 21 receives the voltage signal Vout from the amplifier circuit 11 and converts the voltage signal Vout from an analog signal into a digital signal.

The signal processing unit 3 performs arithmetic operations on the digital signal from the A/D conversion circuit 21. The signal processing unit 3 includes a microcomputer 31, a display unit 32, and a communication unit 33. The microcomputer 31 stores the digital signal in an internal memory (not illustrated) and also analyzes the digital signal and stores the analysis results (for example, the types of the body movement, the number of the body movements, and the size of the body movements) in the memory. Note that the microcomputer 31 may display the analysis results on the display unit 32, or transmit the analysis results from the communication unit 33 to, for example, an external server (not illustrated).

Figure 3:
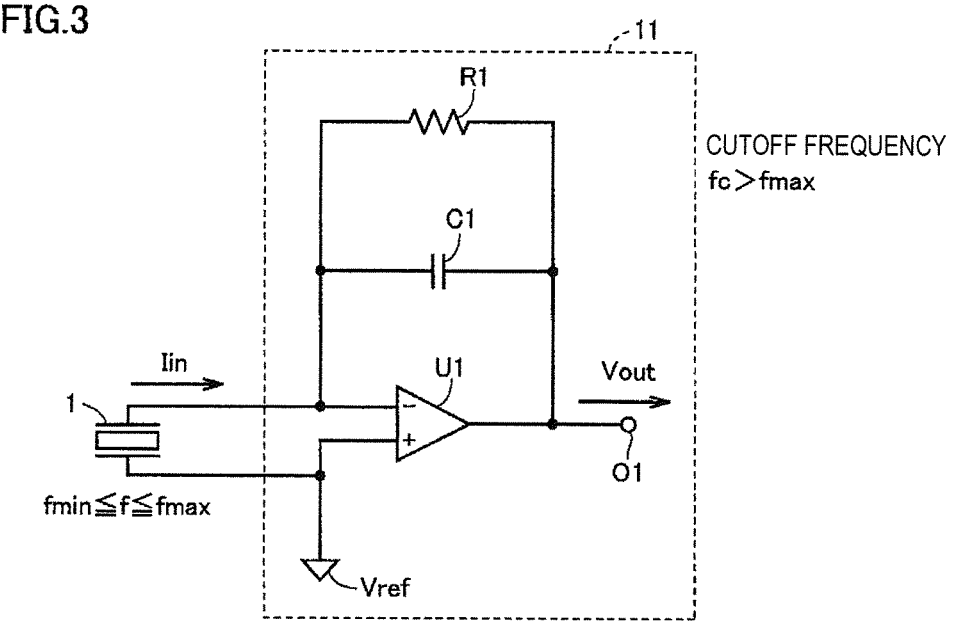
FIG. 3 is a circuit diagram illustrating the configurations of the charge output sensor and amplifier circuit illustrated in FIG. 2.

FIG. 3 is a circuit diagram illustrating the configuration of the amplifier circuit 11 illustrated in FIG. 2. Referring to FIG. 3, the amplifier circuit 11 includes the operational amplifier U1, the resistor R1, the capacitor C1, and the output unit O1. The band of a frequency f of the charge signal Iin is represented by fmin≤f≤fmax.

The operational amplifier U1 includes an inverting input terminal, a non-inverting input terminal, and an output terminal. The piezoelectric device 1 is electrically connected between the non-inverting input terminal and the inverting input terminal of the operational amplifier U1. The inverting input terminal receives the charge signal Iin from one end of the piezoelectric device 1. The non-inverting input terminal and the other end of the piezoelectric device 1 are electrically connected to the reference potential Vref. The voltage signal Vout is outputted from the output terminal.

The resistor R1 is electrically connected between the inverting input terminal and the output terminal of the operational amplifier U1. The capacitor C1 is connected in parallel with the resistor R1.

In the frequency band of the charge signal Iin, the resistance value of the resistor R1 and the capacitance value of the capacitor C1 are set such that the absolute value of the impedance of the resistor R1 is lower than the absolute value of the impedance of the capacitor C1. As a result, the amplifier circuit 11 can be made to operate as a trans-impedance amplifier circuit.

When described in more detail, the piezoelectric device 1 is deformed in accordance with the body movement of the subject 8. The piezoelectric body is polarized in accordance with the amount of the deformation of the piezoelectric device 1. When the piezoelectric body is polarized, a potential difference is generated between the electrodes between which the piezoelectric body is sandwiched. This potential difference causes a current to flow through a wiring line connecting the piezoelectric device 1 to the amplifier circuit 11. A change in the amount of a charge generated in the form of a current described above is called the charge signal Iin. In the frequency band of the charge signal Iin, the absolute value of the impedance of the resistor R1 is sufficiently lower than the absolute value of the impedance of the capacitor C1. Hence, the whole current flows through the resistor R1. The voltage across the resistor R1 is equal to the resistance value of the resistor R1 multiplied by the value of the current flowing through the resistor R1. Hence, the current can be converted into a voltage by using the amplifier circuit 11.

The amount of a charge generated in the piezoelectric body by the polarization of the piezoelectric body can change with time in accordance with the body movement of a subject. The amplifier circuit 11 amplifies the charge signal Iin and converts the charge signal Iin into the voltage signal Vout.

The trans-impedance amplifier circuit has the frequency characteristics of a low pass filter (LPF). The resistance value of the resistor R1 and the capacitance value of the capacitor C1 are adjusted such that the cutoff frequency fc ($=1/2\pi\tau$, $\tau=R1 \times C1$) of the LPF is in a frequency range above the frequency band of the charge signal Iin (fc>fmax). In other words, the cutoff frequency fc which is determined in accordance with the product of the resistance value of the resistor R1 and the capacitance value of the capacitor C1 is set so as to be higher than the frequency band of the charge signal Iin.

Figure 4:
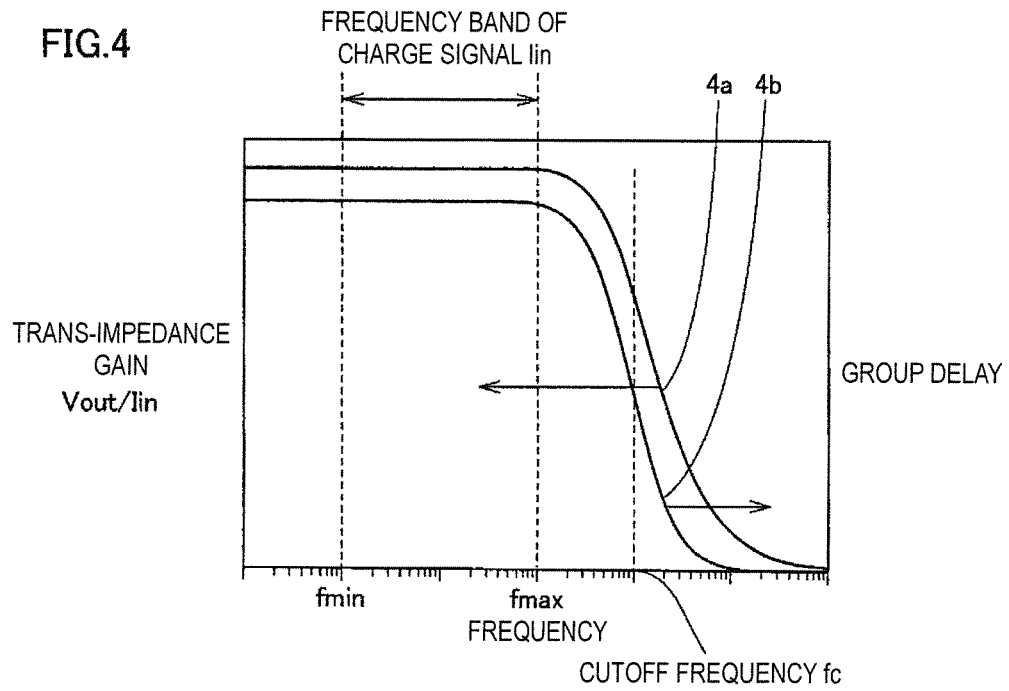
FIG. 4 is a diagram illustrating the frequency characteristics of the trans-impedance gain and the frequency characteristics of the group delay of the amplifier circuit illustrated in FIG. 3.

FIG. 4 is a diagram illustrating the frequency characteristics of the trans-impedance gain and the frequency characteristics of the group delay of the amplifier circuit 11 illustrated in FIG. 3. The horizontal axis represents the frequency of the charge signal Iin using a logarithmic scale.

The vertical axes represent the trans-impedance gain (the ratio of the voltage value of the voltage signal Vout to the current value of the charge signal Iin, refer to the left vertical axis) and the group delay of the voltage signal Vout with respect to the charge signal Iin (refer to the right vertical axis). A curve 4a represents the frequency characteristics of the trans-impedance gain. A curve 4b represents the frequency characteristics of the group delay.

The group delay suddenly changes near the cutoff frequency fc. However, the group delay is constant in a frequency band below the vicinity of the cutoff frequency fc. As described above, the cutoff frequency fc is located in a frequency range above the frequency band of the charge signal Iin. As a result, the frequency characteristics of the group delay can be made approximately flat over the whole frequency band of the charge signal Iin. In other words, the group delay becomes approximately constant, almost independently of the frequency of the charge signal Iin. Hence, according to the first embodiment, the frequency characteristics of the group delay of an amplifier circuit that amplifies a signal from a charge output sensor can be improved.

Second Embodiment

In a second embodiment, a swallowing detection apparatus will be described as a specific example of the body movement detection apparatus described in the first embodiment.

Figure 5:
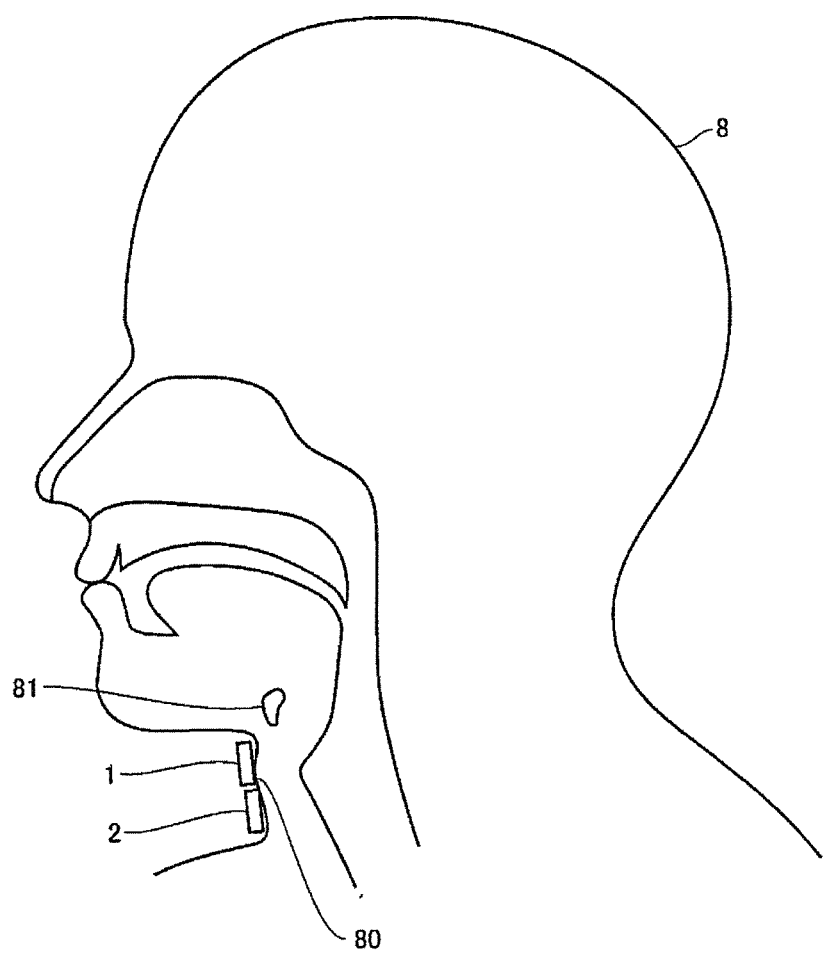
FIG. 5 is a schematic diagram illustrating the installation state of a detection apparatus according to a second embodiment of the present disclosure.

FIG. 5 is a schematic diagram illustrating the installation state of a swallowing detection apparatus according to the second embodiment of the present disclosure. Referring to FIG. 5, a swallowing detection apparatus 200 is an apparatus used for evaluating the number and strength of swallowing actions of the subject 8. Piezoelectric devices 1 and 2 are mounted near a larynx 80 of the subject 8.

A hyoid bone 81 is considerably displaced upward during a swallowing time. As a result, the larynx 80 is lifted upward. The piezoelectric device 1 is deformed as a result of the movement of the larynx 80. Hence, the piezoelectric device 1 can detect the displacement of the hyoid bone 81. The amount of the charge of the piezoelectric device 1 changes in accordance with the amount of displacement of the hyoid bone 81. In the present embodiment, a charge signal indicating a change in the amount of the charge corresponding to the amount of the deformation of the piezoelectric device 1 is called a displacement signal I1 (refer to FIG. 6). The frequency band of the displacement signal I1 is, for example, about 100 mHz to 10 Hz.

Upon detection of the sound (swallowing sound) generated at the time of swallowing, the amount of the charge of the piezoelectric device 2 changes in accordance with the magnitude of the sound level. In the present embodiment, a charge signal indicating a change in the amount of the charge corresponding to the amount of the deformation of the piezoelectric device 2 is called an audio signal Q2 (refer to FIG. 6). The frequency band of the audio signal Q2 is higher than the frequency band of the displacement signal I1 and is, for example, about 100 Hz to 10 kHz.

For example, a piezoelectric film whose material is plastic polyvinylidene difluoride (PVDF) can be employed for the piezoelectric device 1. For example, a piezoelectric film microphone whose material is plastic PVDF may be employed for the piezoelectric device 2. However, the configurations of the piezoelectric devices 1 and 2 are not limited to these, and the material of the piezoelectric devices 1 and 2 may be lead zirconate titanate (PZT), barium titanate (BaTiO3), or the like.

By employing two piezoelectric devices in this way, the number and strength of swallowing actions can be determined with higher accuracy. For example, in the case where both the displacement signal I1 from the piezoelectric device 1 and the audio signal Q2 from the piezoelectric device 2 are detected, the detection result is determined to be swallowing. On the other hand, in the case where only the audio signal Q2 is detected, the sound or voice can be determined to be a breathing sound. On the contrary, in the case where only the displacement signal I1 is detected, the detection result can be determined to be erroneous detection (for example, an artifact).

Note that the piezoelectric device 1 corresponds to the "first sensor" according to the present disclosure. The "detection object" and the "detection result" of the piezoelectric device 1 relate to the displacement of the hyoid bone at the time of swallowing. The displacement signal I1 corresponds to the "first signal component" according to the present disclosure. The piezoelectric device 2 corresponds to the "second sensor" according to the present disclosure. The "detection object" and the "detection result" of the piezoelectric device 2 relate to a swallowing sound. The audio signal Q2 corresponds to the "second signal component" according to the present disclosure.

Figure 6:
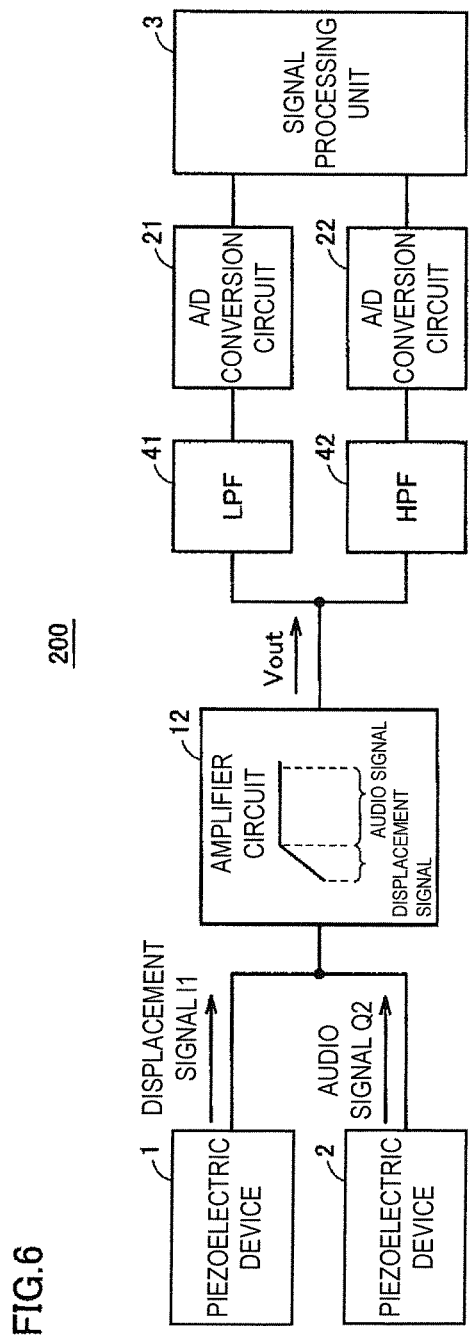
FIG. 6 is a block diagram schematically illustrating the configuration of the detection apparatus illustrated in FIG. 5.
Figure 7:
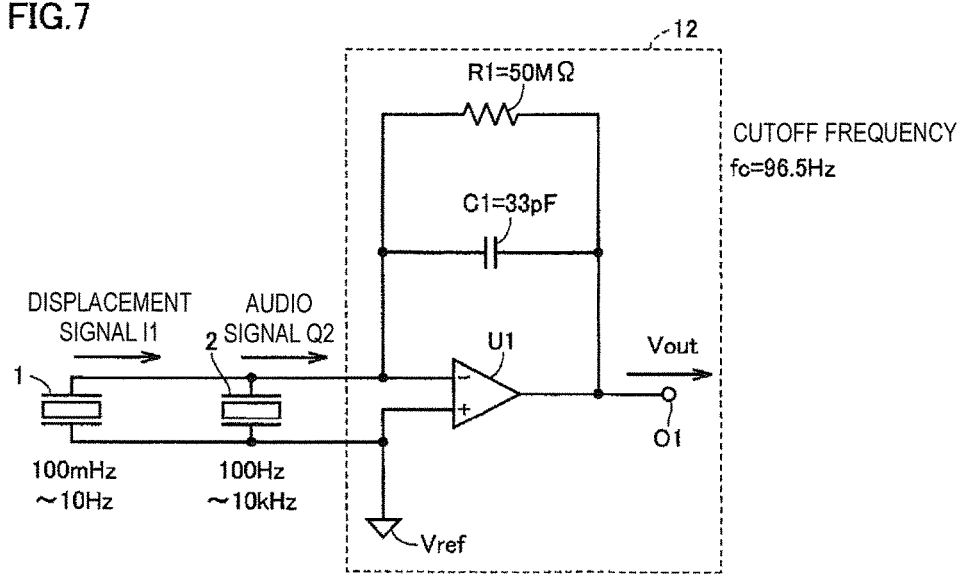
FIG. 7 is a circuit diagram illustrating the configurations of the charge output sensors and amplifier circuit illustrated in FIG. 6.

FIG. 6 is a block diagram schematically illustrating the configuration of the swallowing detection apparatus 200 illustrated in FIG. 5. FIG. 7 is a circuit diagram illustrating the configurations of the piezoelectric devices 1 and 2 and an amplifier circuit 12 illustrated in FIG. 6.

Referring to FIG. 6 and FIG. 7, the swallowing detection apparatus 200 includes the piezoelectric devices 1 and 2, the amplifier circuit 12, a low pass filter (LPF) 41, a high pass filter (HPF) 42, A/D conversion circuits 21 and 22, and the signal processing unit 3.

In the amplifier circuit 12, the resistance value of the resistor R1 is set to, for example, 50 MΩ. The capacitance value of the capacitor C1 is set to, for example, 33 pF. Hence, the time constant τ of the amplifier circuit 12 is calculated as τ=R1×C1=1.65 ms. A variable resistor may be employed as the resistor R1 to adjust the time constant τ. Alternatively, a variable capacitor may be employed as the capacitor C1.

The circuit configuration of the trans-impedance amplifier circuit and the circuit configuration of the charge amplifier circuit are the same in that the resistor R1 and the capacitor C1 are connected in parallel with each other between the non-inverting input terminal and the output terminal of the operational amplifier U1.

However, a current flows through the resistor R1 in the trans-impedance amplifier circuit. As a result, the current is converted into a voltage. In other words, the resistor R1 is a configuration component for converting a current into a voltage in the trans-impedance amplifier. On the other hand, the capacitor C1 is provided to secure negative feedback stability.

In contrast, a charge is stored in the capacitor C1 in the charge amplifier circuit. As a result, the charge is converted into a voltage. In other words, the capacitor C1 is a configuration component for converting a charge into a voltage in the charge amplifier. On the other hand, the resistor R1 is provided to discharge the charge stored in the capacitor C1 with the time constant τ.

An impedance $Z_R$=R of the resistor R1 is constant independent of the frequency of the displacement signal I1 or the audio signal Q2. On the other hand, an impedance $Z_C$=1/(j×2πf×C1) of the capacitor C1 changes in accordance with the frequency f of a signal input to the operational amplifier U1. Ideally, the impedance $Z_C$ of the capacitor C1 is inversely proportional to the frequency of a signal input to the operational amplifier U1.

It is determined whether the amplifier circuit 12 operates as a trans-impedance amplifier circuit or a charge amplifier circuit on the basis of which of the absolute value $|Z_R|$ of the impedance $Z_R$ of the resistor R1 and the absolute value $|Z_C|$ of the impedance $Z_C$ of the capacitor C1 is lower than the other in the frequency band of the displacement signal I1 or the audio signal Q2. In the case where the absolute value $|Z_R|$ of the impedance $Z_R$ of the resistor R1 is lower than the absolute value $|Z_C|$ of the impedance $Z_C$ of the capacitor C1, the amplifier circuit 12 operates as a trans-impedance amplifier circuit. On the other hand, in the case where the absolute value $|Z_C|$ of the impedance $Z_C$ of the capacitor C1 is lower than the absolute value $|Z_R|$ of the impedance $Z_R$ of the resistor R1, the amplifier circuit 12 operates as a charge amplifier circuit.

The resistance value of the resistor R1 and the capacitance value of the capacitor C1 are set such that the absolute value $|Z_R|$ of the impedance $Z_R$ of the resistor R1 is lower than the absolute value $|Z_C|$ of the impedance $Z_C$ of the capacitor C1 in the frequency band (100 mHz to 10 Hz) of the displacement signal I1.

When described using numerical values, the absolute value $|Z_R|$ of the impedance $Z_R$ of the resistor R1 is 50 MΩ. On the other hand, the absolute value $|Z_C|$ of the impedance $Z_C$ of the capacitor C1 becomes minimum in the case where the frequency of the displacement signal I1 is 10 Hz (maximum value). The minimum value of the absolute value $|Z_C|$ of the impedance $Z_C$ is $1/(2\pi \times 10 \times 33 \times 10^{-12})$=482 MΩ.

In this way, in the frequency band of the displacement signal I1, the absolute value $|Z_R|$ of the impedance $Z_R$ of the resistor R1 is lower than the absolute value $|Z_C|$ of the impedance $Z_C$ of the capacitor C1. Hence, the amplifier circuit 12 operates as a trans-impedance amplifier circuit for the displacement signal I1. In other words, the amplifier circuit 12 amplifies the displacement signal I1 and converts it into the voltage signal Vout.

When operating as the trans-impedance amplifier circuit, the amplifier circuit 12 has the frequency characteristics of an LPF. The cutoff frequency fc of this LPF is set so as to be higher than the frequency band (100 mHz to 10 Hz) of the displacement signal I1. In the present embodiment, the cutoff frequency fc is fc=$1/2\pi\tau$=96.5 Hz.

On the other hand, in the frequency band (100 Hz to 10 kHz) of the audio signal Q2, the resistance value of the resistor R1 and the capacitance value of the capacitor C1 are set such that the absolute value $|Z_C|$ of the impedance $Z_C$ of the capacitor C1 is lower than the absolute value $|Z_R|$ of the impedance $Z_R$ of the resistor R1.

When described using numerical values, the absolute value $|Z_R|$ of the impedance $Z_R$ of the resistor R1 is 50 MΩ. On the other hand, the absolute value $|Z_C|$ of the impedance $Z_C$ of the capacitor C1 becomes maximum in the case where the frequency of the audio signal Q2 is 100 Hz (minimum value). The maximum value of the absolute value $|Z_C|$ of the impedance $Z_C$ is $1/(2\pi \times 100 \times 33 \times 10^{-12})$=48 MΩ.

In this way, in the frequency band of the audio signal Q2, the absolute value $|Z_C|$ of the impedance $Z_C$ of the capacitor C1 is lower than the absolute value $|Z_R|$ of the impedance $Z_R$ of the resistor R1. Hence, the amplifier circuit 12 operates as a charge amplifier circuit for the audio signal Q2. In other words, the amplifier circuit 12 amplifies the audio signal Q2 and converts it into the voltage signal Vout.

When operating as a charge amplifier circuit, the amplifier circuit 12 has the frequency characteristics of an HPF. The cutoff frequency fc (=96.5 Hz) of this HPF is set so as to be lower than the frequency band (100 Hz to 10 kHz) of the audio signal Q2. The rest of the configuration of the amplifier circuit 12 is equivalent to the configuration of the amplifier circuit 11 (refer to FIG. 3) and, hence, the detailed description thereof is not repeated.

As described above, the amplifier circuit 12 operates as a trans-impedance amplifier circuit in the frequency band of the displacement signal I1, whereas the amplifier circuit 12 operates as a charge amplifier circuit in the frequency band of the audio signal Q2. In other words, by using the common amplifier circuit, the respective charge signals in the two frequency bands can be converted into voltage signals. As a result, the size and cost of a swallowing detection apparatus can be reduced compared with the case where an amplifier circuit for converting the displacement signal I1 into the voltage signal Vout and an amplifier circuit for converting the audio signal Q2 into the voltage signal Vout are independently provided.

The voltage signal Vout includes a signal component based on the displacement signal I1 and a signal component based on the audio signal Q2. In order to isolate these signal components, the LPF 41 and the HPF 42 are provided.

The LPF 41 allows the voltage signal Vout having the frequency band of the displacement signal I1 to pass therethrough. The HPF 42 allows the voltage signal Vout having the frequency band of the audio signal Q2 to pass therethrough. In the present embodiment, the LPF 41 allows a signal component with a frequency of 10 Hz or below to pass therethrough. The HPF 42 allows a signal component with a frequency of 100 Hz or above to pass therethrough.

The A/D conversion circuit 21 receives the voltage signal Vout having the frequency band of the displacement signal I1 from the LPF 41, and converts the signal component from an analog signal into a digital signal. The A/D conversion circuit 22 receives the voltage signal Vout having the frequency band of the audio signal Q2 from the HPF 42, and converts the signal component from an analog signal into a digital signal. Both of the digital signals from the A/D conversion circuits 21 and 22 are outputted to the signal processing unit 3. The rest of the configuration of the swallowing detection apparatus 200 is equivalent to the corresponding configuration of the body movement detection apparatus 100 (refer to FIG. 2) and, hence, the detailed description thereof is not repeated.

The reason why the LPF 41 and the HPF 42 are provided will be described from another point of view. In a detection apparatus that detects living matter information such as a body movement, a small signal is often handled. Further, the frequency (50 HZ or 60 Hz in Japan) of a commercial power supply is close to the frequency of a signal. Hence, in the case where noise with the frequency of the commercial power supply is superimposed on the signal, the signal will be considerably influenced by the noise. When described in more detail, in the case where the electrical outlet is provided on a wall surface, the potentials of the wall surface and a floor slightly fluctuate at the frequency of the commercial power supply. Hence, as a result of the subject 8 being capacitively coupled with the wall surface or the floor, noise may be superimposed on the signal even when the power supply of the swallowing detection apparatus 200 is not a commercial power supply. Hence, the detection accuracy of the swallowing detection apparatus 200 may be decreased.

According to the present embodiment, noise whose frequency band is 10 Hz to 100 Hz is removed. In other words, noise which varies at the frequency of a commercial power supply can be removed. This allows the detection accuracy of a swallowing detection apparatus to be enhanced.

Figure 8:
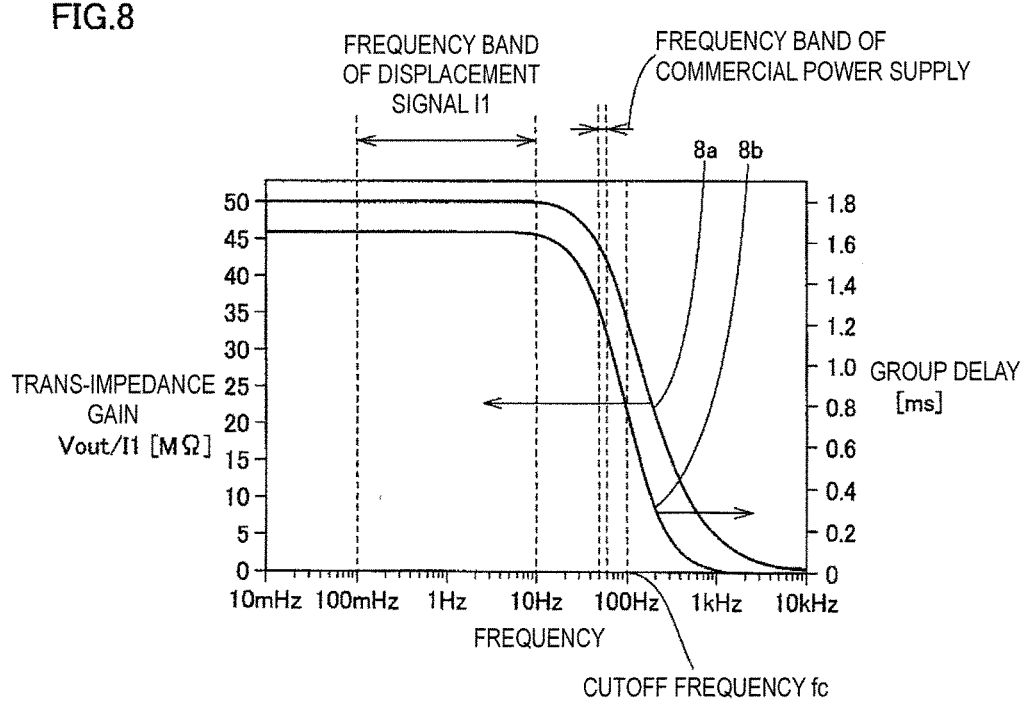
FIG. 8 is a diagram illustrating examples of the frequency characteristics of the trans-impedance gain and the frequency characteristics of the group delay regarding the displacement signal illustrated in FIG. 7.

FIG. 8 is a diagram illustrating examples of the frequency characteristics of the trans-impedance gain and the frequency characteristics of the group delay regarding the displacement signal I1 illustrated in FIG. 7. Referring to FIG. 8, FIG. 8 is compared with FIG. 4.

The frequency characteristics of the trans-impedance gain and the frequency characteristics of the group delay are approximately flat over the whole frequency band of the displacement signal I1. Hence, according to the present embodiment, the frequency characteristics of the trans-impedance gain and the frequency characteristics of the group delay can be improved.

It can be seen that the value of the trans-impedance gain in the region where the frequency characteristics of the trans-impedance gain are flat is determined by the resistance value (50 MΩ) of the resistor R1 (Vout/I1=R1). It can be supported also from this point of view that the amplifier circuit 12 is operating as a trans-impedance amplifier circuit.

Figure 14:
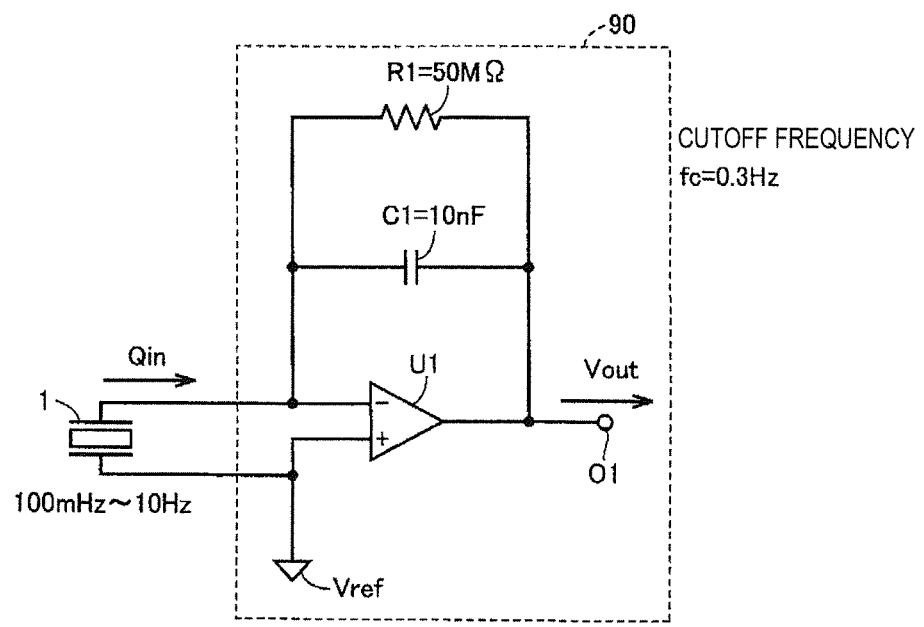
FIG. 14 is a circuit diagram illustrating an example of the configuration of a general charge amplifier circuit.
Figure 15:
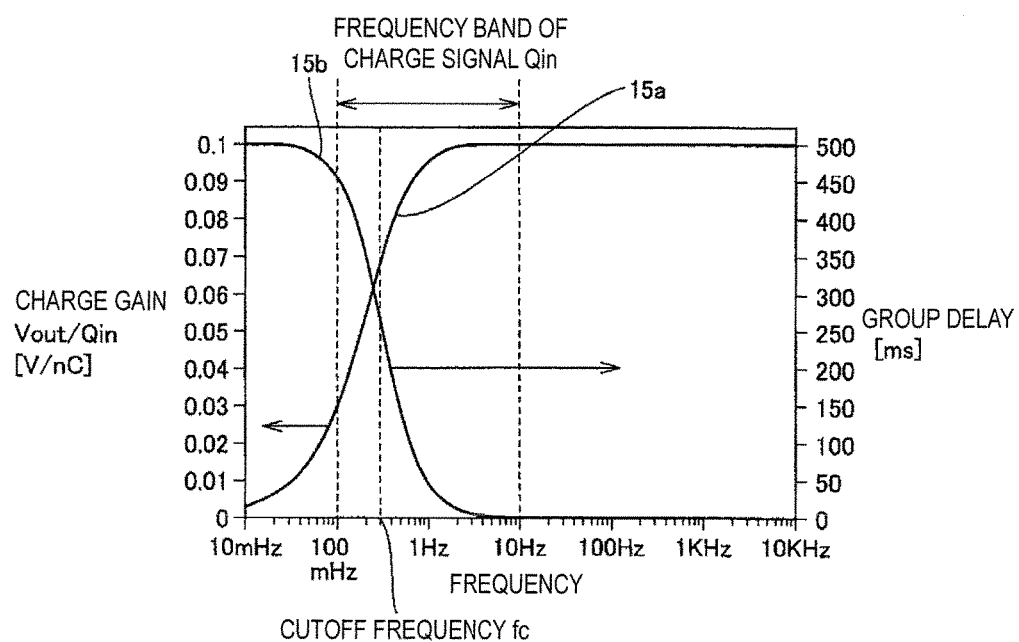
FIG. 15 is a diagram illustrating examples of the frequency characteristics of the charge gain and the frequency characteristics of the group delay of the charge amplifier circuit illustrated in FIG. 14.

Further, when the frequency characteristics of the group delay of the amplifier circuit 12 are compared with those of the charge amplifier circuit 90 (refer to FIG. 14), the frequency band of the displacement signal I1 is the same as the frequency band (refer to FIG. 15) of the charge signal Iin. In this frequency band, the maximum value of the group delay in the charge amplifier circuit 90 is about 450 ms (refer to FIG. 15). On the other hand, the maximum value of the group delay in the amplifier circuit 12 is about 1.6 ms. In this way, according to the present embodiment, by making an amplifier circuit operate as a trans-impedance amplifier circuit, the responsiveness of the amplifier circuit can be enhanced. The reason for this will be described in detail below.

The group delays D(f) of the charge amplifier circuit and the trans-impedance amplifier circuit realized by the common circuit configuration are both given by the following Equation (1).

$$D(f) = \tau / \{1 + (2\pi \times f \times \tau)^2\} \quad (1)$$

It can be seen from Equation (1) that the group delay D(f) can be decreased by decreasing the time constant τ. The time constant τ of the amplifier circuit 12 is τ=1.65 ms (=50 MΩ×33 pF). On the other hand, the time constant τ of the charge amplifier circuit 90 is τ=500 ms (=50 MΩ×10 nF). In other words, compared with the charge amplifier circuit 90, the group delay time is about 312 times smaller in the trans-impedance amplifier circuit illustrated in FIG. 7. Hence, the responsiveness of the amplifier circuit 12 is enhanced by making the amplifier circuit 12 operated as an impedance amplifier circuit.

For example, in the case where a group delay of about 450 ms is generated, the subject 8 may feel that the voltage signal Vout is outputted slightly later than the body movement. On the other hand, the subject 8 can feel that the voltage signal Vout is outputted immediately after the body movement when the group delay is about 1.6 ms. Hence, according to the present embodiment, the swallowing detection apparatus 200 can be used without stress since the swallowing detection apparatus 200 has good responsiveness.

Note that the cutoff frequency fc is adjusted to a frequency higher than the frequency band of the displacement signal I1. In other words, since the time constant τ is made small, the resistor R1 having a high resistance value need not be used. Hence, it provides such an effect that the frequency characteristics of the trans-impedance gain and the frequency characteristics of the group delay are improved and the responsiveness is improved without causing a problem of an increase in the size or cost of the resistor R1.

Figure 9:
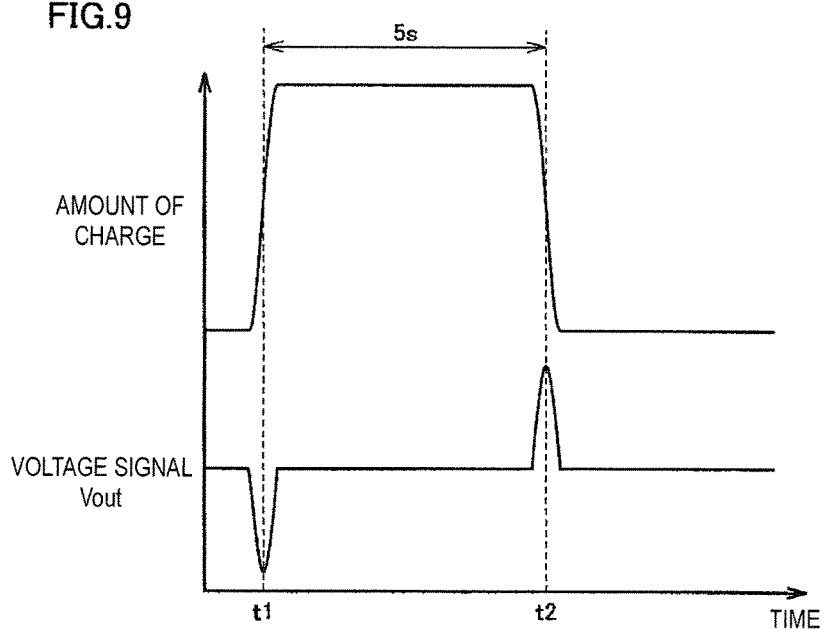
FIG. 9 is a diagram illustrating an example of the waveform of the voltage signal illustrated in FIG. 7.

FIG. 9 is a diagram illustrating an example of the waveform of the voltage signal Vout illustrated in FIG. 7. Referring to FIG. 9, the horizontal axis is a time axis. The vertical axis represents the amount of a charge and a voltage.

Referring to FIG. 9, the piezoelectric device 1 outputs the displacement signal I1 during, for example, five seconds from time t1 to time t2. The voltage signal Vout is a signal which is a derivative of the displacement signal I1. Hence, the voltage signal Vout changes in the form of pulses before and after time t1 and time t2 when the amount of a charge considerably varies with time. In other words, an output waveform is obtained in which times (the falling time t1 and rising time t2 of the displacement signal I1 in FIG. 9) corresponding to large changes in the amount of a charge are emphasized.

Figure 10:
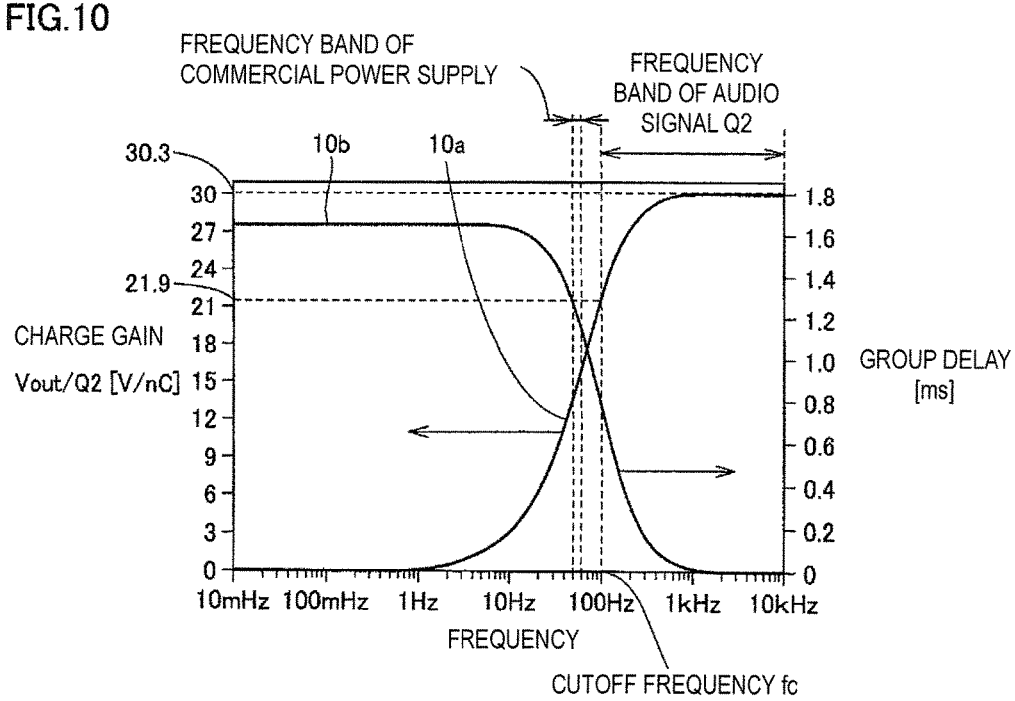
FIG. 10 is a diagram illustrating examples of the frequency characteristics of the charge gain and the frequency characteristics of the group delay regarding the audio signal illustrated in FIG. 7.

FIG. 10 is a diagram illustrating examples of the frequency characteristics of the charge gain and the frequency characteristics of the group delay regarding the audio signal Q2 illustrated in FIG. 7. Referring to FIG. 10, the horizontal axis represents the frequency of the audio signal Q2 using a logarithmic scale. The vertical axes represent the charge gain (the ratio of the voltage value of the voltage signal Vout to the amount of the charge of the audio signal Q2, refer to the left vertical axis) and the group delay (refer to the right vertical axis) of the voltage signal Vout with respect to the audio signal Q2. A curve 10a represents the frequency characteristics of the charge gain. A curve 10b represents the frequency characteristics of the group delay.

In the example illustrated in FIG. 10, the frequency band of the audio signal Q2 is 100 Hz to 10 kHz. The cutoff frequency fc of the amplifier circuit 12 is 96.5 Hz. In other words, the cutoff frequency fc is located in a frequency range below the frequency band of the audio signal Q2. Hence, the frequency characteristics of the group delay negligibly change over the whole range of the frequency band of the audio signal Q2. Specifically, the group delay in a frequency band of 1 kHz or above is approximately zero. Further, when the frequency is 100 Hz, the group delay is at most about 0.8 ms.

Further, the charge gain is about 30.3 (V/nC) in a frequency band above or equal to 500 Hz. This value is about 300 times higher than the charge gain (refer to FIG. 15) of the charge amplifier circuit 90 illustrated in FIG. 14. The charge gain in the case where the frequency is 100 Hz is also about 21.9 (V/nC). In this way, the frequency characteristics of the charge gain do not change so much over the whole range of the frequency band of the audio signal Q2, either.

As described above, it can be seen that in the case where the amplifier circuit 12 is made to operate as a charge amplifier circuit, the frequency characteristics of the group delay and the frequency characteristics of the charge gain can be improved by setting the cutoff frequency fc to a frequency lower than the frequency band of the audio signal Q2.

Further, generally, it is necessary to take several times longer than the time constant until the operation of the amplifier circuit is stabilized after it is activated. This feature can be a problem, particularly in the case where the time constant is large. According to the present embodiment, since the cutoff frequency fc is adjusted to a higher frequency, the time constant is decreased. Hence, a time required until the amplifier circuit is stabilized can be reduced.

Note that to adjust the cutoff frequency fc to a higher frequency (to reduce the time constant τ), it can be thought that the resistance value of the resistor R1 is decreased or the capacitance value of the capacitor C1 is decreased. Ideally, the charge gain is represented by 1/C1. In other words, the charge gain is increased as the capacitance value of the capacitor C1 is decreased. Hence, it is preferable to decrease the capacitance value of the capacitor C1 than to decrease the resistance value of the resistor R1 to adjust the cutoff frequency fc to a higher frequency. When the amplifier circuit 12 (refer to FIG. 7) is compared with the charge amplifier circuit 90 (refer to FIG. 14), the capacitance value of the capacitor C1 is changed from 10 nF to 33 pF, while the resistance value of the resistor R1 is 50 MΩ in both cases.

Further, to increase the detection accuracy of the swallowing detection apparatus 200, a configuration may be considered in which a filter for noise elimination is inserted in a stage prior to the amplifier circuit 12. However, when such a filter is inserted, the displacement signal I1 (or the audio signal Q2) is delayed and the waveform of the displacement signal I1 is blunted. This influence of the delay is increased as the frequency of the displacement signal I1 is decreased. Hence, it is preferable to shield the piezoelectric device 1, the amplifier circuit 11, or a wiring line connecting the piezoelectric device 1 to the amplifier circuit 11 from noise to suppress the superimposition of the noise on the displacement signal I1. Specifically, for example, the amplifier circuit 12 can be housed in a metal casing (not illustrated). This will allow the responsiveness of the swallowing detection apparatus 200 to be increased since the delay in the displacement signal I1 is not generated.

Note that the "first signal component" according to the present disclosure is not limited to a displacement signal indicating the displacement of a living matter or the environment of the living matter, and may be a signal indicating deformation, a change in weight, and the like. Further, the "second signal component" according to the present disclosure is not specifically limited to an audio signal indicating sound generated by the movement of a living matter, as long as the frequency band of the second signal component is higher than the frequency band of the "first signal component". A "sound" includes an ultra low frequency sound (for example, a sound having a frequency lower than 20 Hz) or a supersonic wave (for example, a sound having a frequency higher than 20 kHz), not limited to a sound in the audible range (for example, 20 Hz to 20 kHz) of a person.

Third Embodiment

In a third embodiment, a cough detection apparatus will be described as another specific example of the body movement detection apparatus 100.

Figure 11:
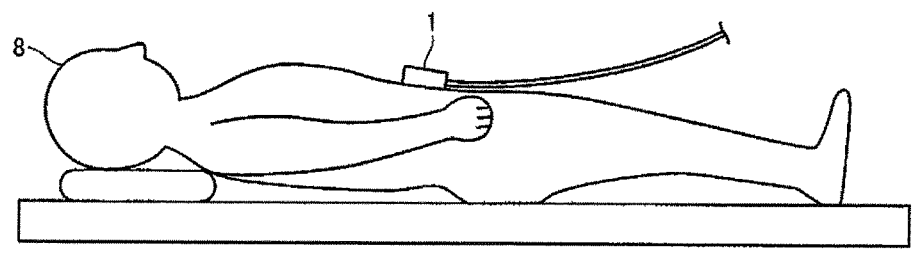
FIG. 11 is a schematic diagram illustrating the installation state of a detection apparatus according to a third embodiment of the present disclosure.

FIG. 11 is a schematic diagram illustrating the installation state of a cough detection apparatus according to a third embodiment of the present disclosure. Referring to FIG. 11, in the cough detection apparatus, the piezoelectric device 1 is preferably mounted on the abdomen, and more preferably mounted near a portion below the diaphragm. As a result of the piezoelectric device 1 being mounted at this position, it becomes possible to detect a weak cough. Further, accuracy is enhanced because erroneous detection is unlikely to be generated compared with the case where the piezoelectric device 1 is mounted near the throat.

In the third embodiment, the displacement signal I1 and the audio signal Q2 are outputted from the single piezoelectric device 1. When described more specifically, a muscle (respiratory muscle or the like) shrinks due to a cough. The piezoelectric device 1 detects the displacement of the abdomen due to this shrinkage and outputs the displacement signal I1. Further, air in contact with the abdomen vibrates at the time of a cough and, hence, a sound is generated. The piezoelectric device 1 detects this sound and outputs the audio signal Q2. In this way, by obtaining signals having different frequency bands using a single piezoelectric device, the cost and size of a detection apparatus can be reduced, compared with the case where piezoelectric devices are installed for the respective frequency bands.

Note that the "detection object" and the "detection result" of the piezoelectric device 1 relate to the displacement of an abdomen. The "detection object" and the "detection result" of the piezoelectric device 2 relate to a sound generated due to the displacement of the abdomen.

Figure 12:
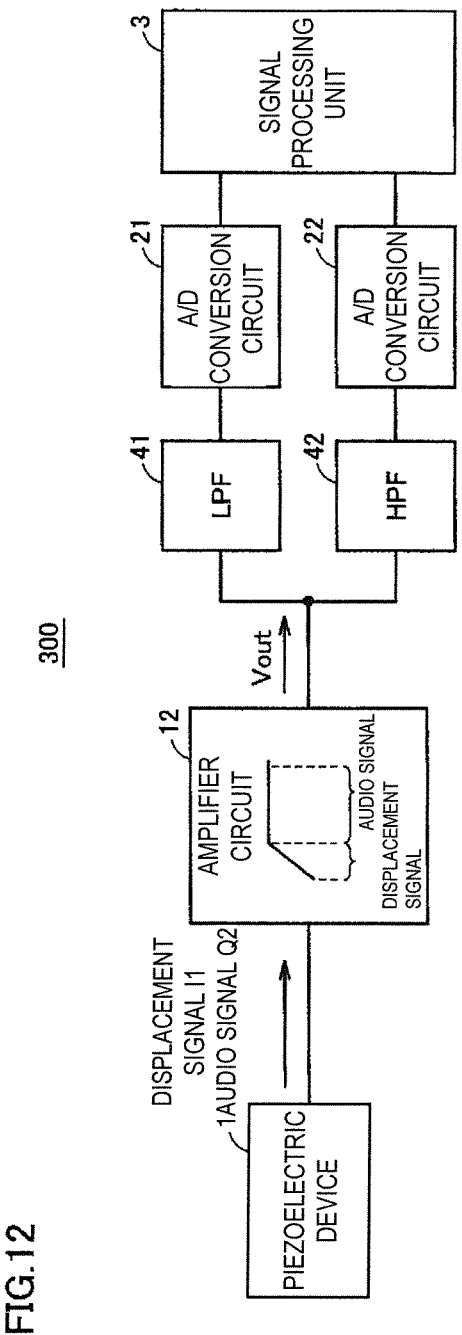
FIG. 12 is a block diagram schematically illustrating the configuration of the detection apparatus illustrated in FIG. 11.

FIG. 12 is a block diagram schematically illustrating the configuration of a cough detection apparatus 300 illustrated in FIG. 11. Referring to FIG. 12, the frequency bands of the displacement signal I1 and the audio signal Q2 in the detection of a cough are approximately the same as those in the detection of swallowing. Hence, for example, the amplifier circuit 12 (refer to FIG. 7) which is the same as that of the swallowing detection apparatus 200 can be utilized. The rest of the configuration of the cough detection apparatus 300 is equivalent to the corresponding configuration of the swallowing detection apparatus 200 (refer to FIG. 6) and, hence, the detailed description thereof is not repeated.

The number of occurrences and strength of a cough can be determined with higher accuracy by obtaining the displacement signal I1 and the audio signal Q2. For example, in the case where both of the displacement signal I1 and the audio signal Q2 are detected, the detection result can be determined to be a cough. In the case of a cough, a wave group which is a group of waveforms having a high strength is formed in the audio signal Q2. By analyzing the pattern of this waveform group, the state (for example, a respiratory disease or not) of the subject 8 is determined.

Note that a configuration similar to the cough detection apparatus 300 also allows respiration to be detected. The sound of a cough is larger than the sound of respiration. Hence, in accordance with the strength of the audio signal Q2, a cough and respiration can be distinguished between each other. In the case where only the audio signal Q2 is detected, the detection result can be determined to be an erroneous detection.

In the second embodiment, two piezoelectric devices are used in the swallowing detection apparatus. In the third embodiment, a single piezoelectric device is used in the swallowing detection apparatus. However, the number of piezoelectric devices is not specifically limited, and may be appropriately set in accordance with a detection object. For example, a single or three or more piezoelectric devices may be used in the cough detection apparatus. Alternatively, two or more piezoelectric devices may be used in the cough detection apparatus.

Fourth Embodiment

A body movement can be detected without directly mounting a piezoelectric device on a subject. In a fourth embodiment, a configuration is described in which a piezoelectric device is installed in a vehicle.

Figure 13:
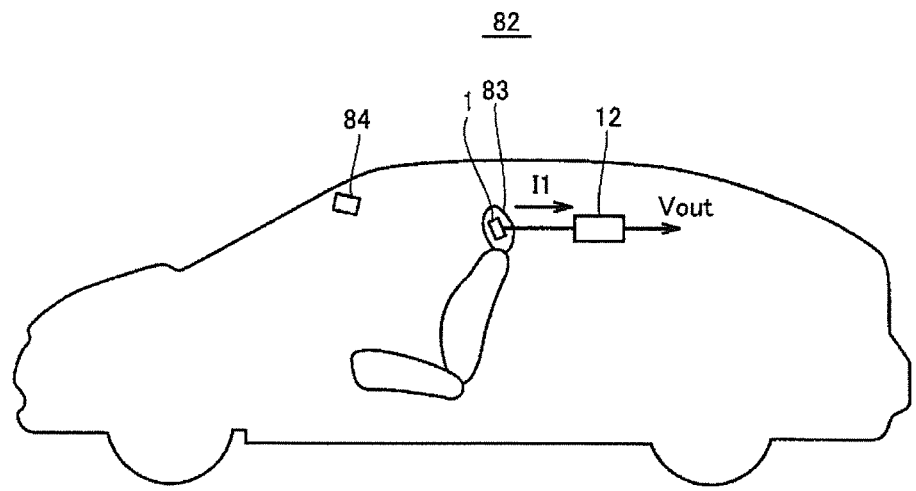
FIG. 13 is a schematic diagram illustrating the installation state of a detection apparatus according to a fourth embodiment of the present disclosure.

FIG. 13 is a schematic diagram illustrating the installation state of a driver state detection apparatus according to a fourth embodiment of the present disclosure. Referring to FIG. 13, in the driver state detection apparatus within a vehicle 82, the piezoelectric device 1 is installed within a headrest 83 of a driver's seat.

In the case where the driver's head presses against the headrest 83, the piezoelectric device 1 is deformed. The piezoelectric device 1 outputs the displacement signal I1 where the amount of a charge changes in accordance with the amount of the deformation.

For example, when the driver is dozing, there may be a case where the head repeatedly moves away from and back to the headrest 83. For example, in the case where the displacement signal I1 is outputted from the piezoelectric device 1, the driver may possibly be sleepy. The amplifier circuit 12 amplifies the displacement signal I1 and converts it into the voltage signal Vout. For example, the electronic control unit (ECU, not illustrated) of the vehicle 82, through processing of the voltage signal Vout from the amplifier circuit 12, may perform processing for calling the driver's attention. Further, for example, the above-described processing may be performed in combination with image information about the driver captured by a camera 84 attached to the front of the vehicle 82.

In this way, a location where the piezoelectric device is installed is not limited to the body of a subject. A "charge output sensor unit (or first and second sensors)" according to the present disclosure may be installed in the environment of a living matter (for example, a subject, a driver, or the like) if a change such as deformation, displacement, change in weight, or the like is generated in the environment of the living matter due to the movement of the living matter.

Note that the "detection object" and the "detection result" of the piezoelectric device 1 relate to the body movement of a driver with respect to the headrest 83 in a driver's seat and a sound generated by the body movement.

The embodiments disclosed here are illustrative in all points and are not considered to be restrictive. The scope of the present disclosure is shown by the claims, and it is intended that all the modifications that have equivalent meanings and that are within the scope of the claims are included.

1, 1a, 2 piezoelectric devices
11, 12, 90 amplifier circuits
U1 operational amplifier
R1 resistor
C1 capacitor
O1 output unit
21, 22 A/D conversion circuits
3 signal processing unit
31 microcomputer
32 display unit
33 communication unit
41 LPF
42 HPF
100 body movement detection apparatus
200 swallowing detection apparatus
300 cough detection apparatus
8 subject
80 larynx
81 hyoid bone
82 vehicle
83 headrest
84 camera

The invention claimed is:

1. A circuit for converting a charge signal into a voltage signal, the charge signal being outputted from a charge output sensor detecting a detection object, and the charge signal indicating a detection result as a change in an amount of a charge,
wherein the charge signal includes a first signal component in a predetermined frequency band,
wherein the circuit comprises:
an operational amplifier including an inverting input terminal receiving the charge signal and an output terminal for outputting the voltage signal;
a resistor electrically connected between the inverting input terminal and the output terminal; and
a capacitor connected in parallel with the resistor,
wherein a resistance value of the resistor and a capacitance value of the capacitor are set such that, for signals in the frequency band of the first signal component, an absolute value of an impedance of the resistor is lower than an absolute value of an impedance of the capacitor,
wherein for signals in the frequency band of the first signal component, a cutoff frequency determined in accordance with a product of the resistance value and the capacitance value is set so as to be higher than the frequency band of the first signal component,
wherein the detection object is a movement of a living matter,
wherein the first signal component is a signal component having an amount of a charge changed in accordance with the movement of the living matter,
wherein the charge signal further includes a second signal component having a frequency band higher than the frequency band of the first signal component,
wherein the resistance value and the capacitance value are set such that, for signals in the frequency band of the second signal component, the absolute value of the impedance of the capacitor is lower than the absolute value of the impedance of the resistor, and
wherein for signals in the frequency band of the second signal component, the cutoff frequency is set so as to be lower than the frequency band of the second signal component.

2. The circuit according to claim 1, wherein the second signal component is a signal component having an amount of a charge changed in accordance with a sound generated by the movement of the living matter.

3. The circuit according to claim 1,
wherein the charge output sensor includes a first sensor and a second sensor, and
wherein the circuit receives the first signal component from the first sensor and the second signal component from the second sensor.

4. A detection apparatus comprising:
the circuit according to claim 1; and
the charge output sensor.

5. The detection apparatus according to claim 4,
wherein the frequency band of the first signal component is lower than a frequency of a commercial power supply,
wherein the frequency band of the second signal component is higher than the frequency of the commercial power supply,
wherein the detection apparatus further comprises:
a low pass filter having a cutoff frequency lower than the frequency of the commercial power supply and allowing the voltage signal in the frequency band of the first signal component to pass therethrough; and
a high pass filter having a cutoff frequency higher than the frequency of the commercial power supply and allowing the voltage signal in the frequency band of the second signal component to pass therethrough.

6. The detection apparatus according to claim 4, wherein the charge output sensor comprises:
   a first sensor for outputting the first signal component; and
   a second sensor for outputting the second signal component.

7. A detection apparatus comprising:
   the circuit according to claim 1; and
   the charge output sensor.

8. A detection apparatus comprising:
   the circuit according to claim 2; and
   the charge output sensor.

* * * * *